United States Patent [19]

Faasse, Jr.

[11] Patent Number: 4,798,208
[45] Date of Patent: Jan. 17, 1989

[54] DIAGNOSTIC ELECTRODE

[76] Inventor: Adrian L. Faasse, Jr., 10499 Braska, SE., Middleville, Mich. 49333

[21] Appl. No.: 129,831

[22] Filed: Dec. 9, 1987

[51] Int. Cl.⁴ ............................................. A61B 5/04
[52] U.S. Cl. ................................... 128/640; 128/798
[58] Field of Search ............... 128/639, 640, 798, 802, 128/803

[56] References Cited

U.S. PATENT DOCUMENTS 3,746,004  7/1973  Jankelson ........................... 128/798
3,842,394  10/1974  Bolduc .............................. 128/639

Primary Examiner—Edward M. Coven
Assistant Examiner—Randy Citrin
Attorney, Agent, or Firm—Price, Heneveld, Cooper, DeWitt & Litton

[57] ABSTRACT

A diagnostic electrode adapted to be affixed to a patient's body for diagnostic medical tests comprising a foam backing layer coated with an adhesive, a tin foil layer bonded to said backing layer and a conductive gel coated on a portion of the tin foil layer. The tin foil layer is of a smaller size than the backing layer and is oriented thereon such that the backing layer forms a U-shaped border around the tin foil layer, to thereby supplement the conductive gel in affixing the electrode to the patient's body. The foam backing layer further provides a surface which a clip, electrically coupled to diagnostic equipment, can securely bite into, in order to securely grip the electrode. A plurality of electrodes are arranged on a release web with their clip tabs intermeshing in side-by-side relation, and extending over a central fold line in the web whereby when the web is folded, the clip tabs are exposed for ease of grasping or securing a lead clip.

16 Claims, 3 Drawing Sheets

DIAGNOSTIC ELECTRODE

BACKGROUND OF THE INVENTION

The present invention pertains to diagnostic electrodes, which are utilized in electrocardiogram examinations.

In such an examination, a diagnostic electrode is electrically connected to the diagnostic equipment and affixed to the patient's body. It is important to not only properly position the electrode on the patient, but also, to do so without excessive handling. Any additional handling of the electrode increases the tendency that the integrity of the electrode may be disturbed, which would in turn, foul the results of the test.

Diagnostic electrodes, in contrast to more expensive monitoring electrodes which include a metal snap mounted to an adhesive coated foam, fabric or plastic web wherein an adhesive coated body adhering surface surrounds the conductive gel coated snap, typically comprise a thin, vinyl or paper backing layer, a tin foil layer and a sticky, conductive gel. The tin foil layer is the middle operative layer which connects the electrode with the equipment. The backing layer conforms to the shape of the tin foil layer and is bonded thereto, to increase the electrode's strength and durability, and to shield its operative portions from damage. The conductive gel is a sticky substance which is applied to the tin foil layer, on a surface opposite to the backing layer, and is used to affix the electrode to the patient. The entire tin foil surface, except for a small end tab, is coated with the gel. The tab is left uncoated to facilitate grasping by the user and attaching of a clip from the diagnostic equipment.

The electrodes are mounted in rows on a release web, which is a plastic or release paper sheet, for storage and dispensing, with their conductive gel layers pressed against the web. Such diagnostic electrodes do not adhere well to the patient and are difficult to use. Only a small amount of space on the electrode is left uncoated whereby the user may grip the electrode to remove it from the release web and attach the clip. To avoid excessive handling during the set up operation, the user may attach the clip to the electrode before removal from the web or after attachment to the patient. An attempt to attach the clip while holding the electrode is a procedure which is prone to error and fouling of the electrode because of the small size of the uncoated tab.

Some users try to attach the clip to the electrode, before the electrode is removed from the web. This is an operation which takes some care and therefore is not accomplished quickly or easily. The user must carefully separate the uncoated tab of the electrode from the release web in order to facilitate attachment of a clip. The user must then peel the electrode from the web, transfer it to the patient, and affix it to the patient's body in the proper position, without dislodging the clip. Due to the thin, somewhat slippery construction of the backing and tin foil layers, the user employing this procedure is faced with a formidable task. As a result, the clip is frequently dislodged during the set up procedure, which then requires the user to start over or attempt to reattach the clip after affixation of the electrode to the body.

Consequently, some users have adopted the procedure of attaching the clip to the electrode subsequent to affixation of the electrode to the body. In this way, the electrode can be more easily removed from the web and attached to the patient in its proper position. Yet, many difficulties face the user employing this procedure, regardless of whether the user intended to subsequently attach the clip or is faced with a reattachment procedure.

In a manner similar to attaching the clip before removal of the electrode from the web, the user must carefully separate the uncoated tab of the electrode from the patient's body, to attach the clip. Additionally, the user also runs the risk of upsetting the proper positioning of the electrode or knocking the electrode completely from the patient. This risk is particularly acute if the patient is sweaty, hairy, moves or is jarred while the user attempts to attach the clip. If this occurs, the user must then restart the test and begin the set up procedure anew.

SUMMARY OF THE INVENTION

In one aspect of the present invention, the release web for the diagnostic electrode is provided with a fold line which allows it to be readily folded back, exposing the clip tab of the electrode and making it extremely easy to secure a lead clip in place while the electrode is still on the release web. In a narrower aspect of the invention a plurality of electrodes are located on the release web so that their clip tabs face one another and are juxtaposed such that all clip tabs overlie the fold line. When the release web is folded, all of the alternating clip tabs project above the fold line in an alternating fashion. This makes the electrodes easy to use and also provides for a very economical construction.

These and other aspects and advantages of the present invention will be more fully understood and appreciated by reference to the appended drawings and Description of the Preferred Embodiment.

DETAILED DESCRIPTION OF THE PREFERRED EMBODIMENT

Figure 1:
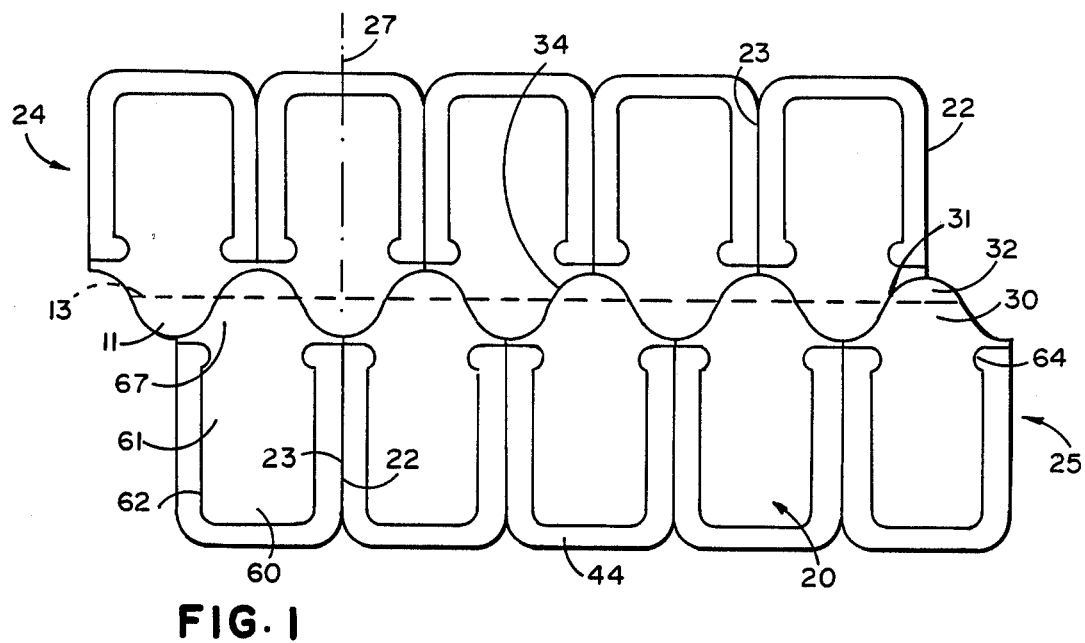
FIG. 1 is a bottom view of the present invention in which the diagnostic electrodes are mounted to the release web.
Figure 2:
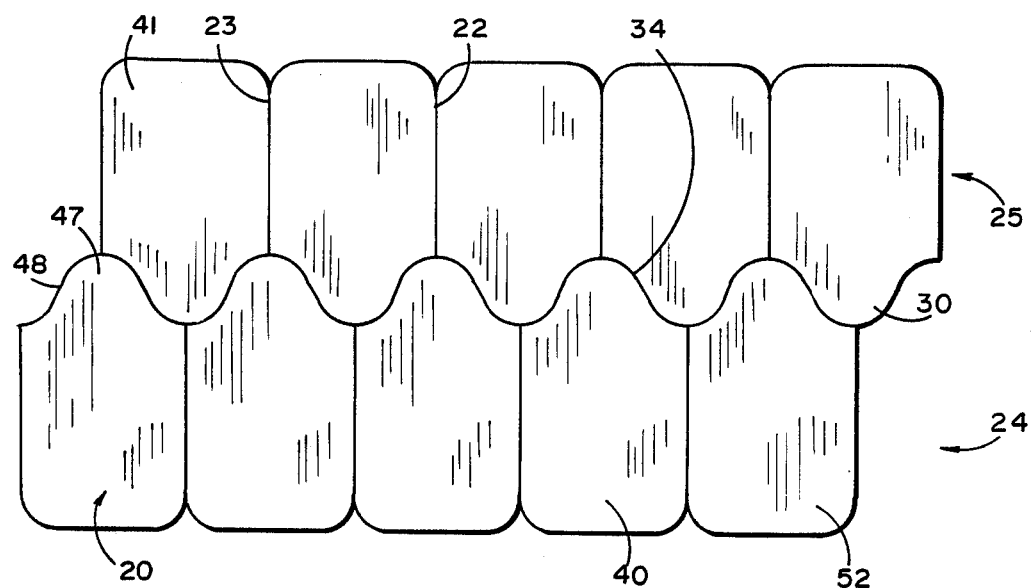
FIG. 2 is a top view of the present invention in which the diagnostic electrodes are mounted to the release web.
Figure 3:
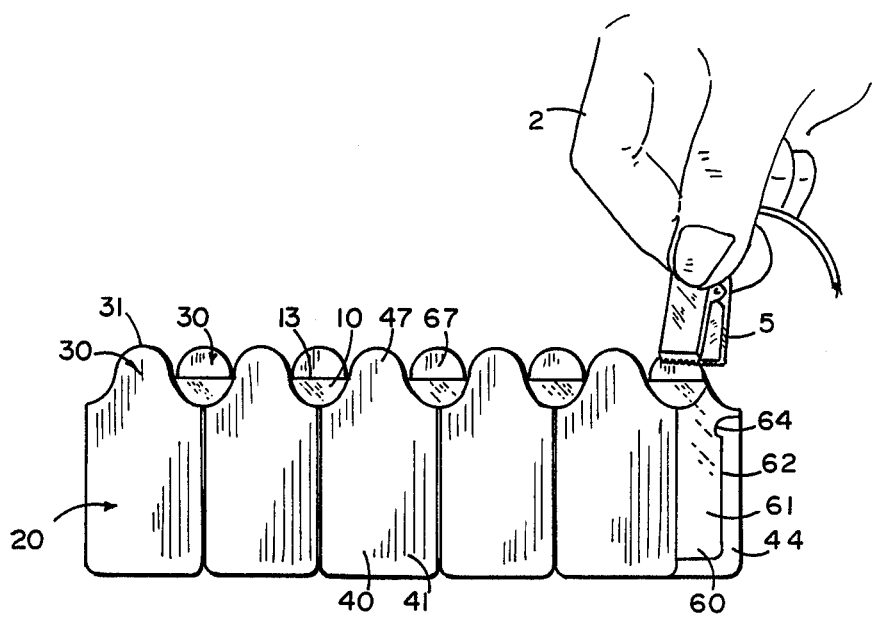
FIG. 3 is a front elevational view of the present invention in which the release web has been folded back to expose the tabs of the electrodes to which a lead clip may be easily attached.
Figure 4:
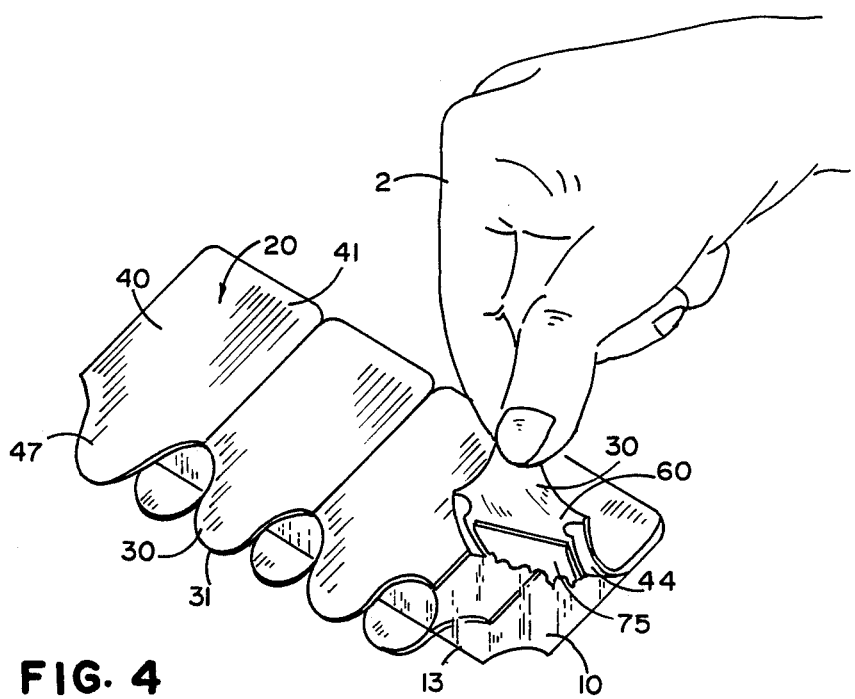
FIG. 4 is a perspective view of the present invention in which the release web has been folded back exposing the tabs of the electrodes so that the electrode may be easily removed from the web.
Figure 5:
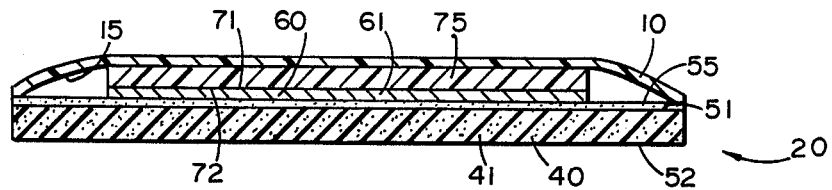
FIG. 5 is an enlarged transverse cross-sectional view of one electrode mounted on the release web.
Figure 6:
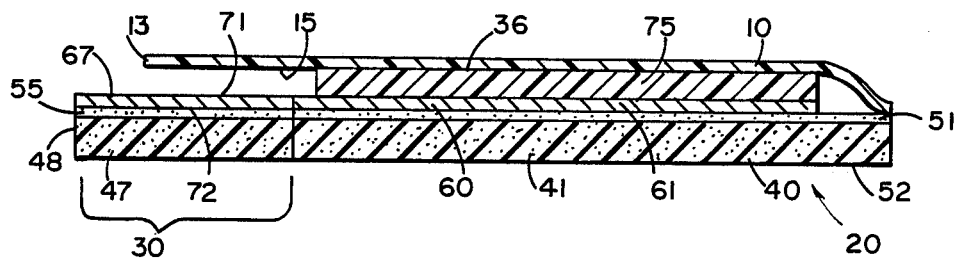
FIG. 6 is an enlarged longitudinal cross-sectional view of one electrode mounted on the release web.
Figure 7:
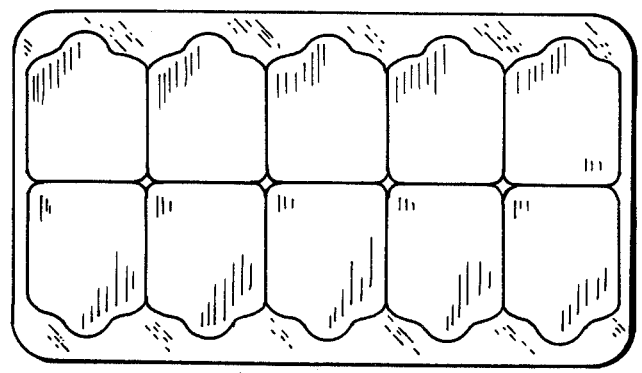
FIG. 7 is an illustration of a prior art device wherein diagnostic electrodes are mounted on a release web.

In the preferred embodiment, diagnostic electrodes 20 are comprised of a foam backing layer 40 provided with an adhesive 55, upon which is mounted a tin foil layer 60 of reduced size which is itself coated with a conductive gel 75 (FIGS. 1, 5 and 6). Foam backing layer 40 provides a surface which clip 5 can bite into and thereby be securely mounted upon tab 30 at one end of electrode 20 so that clip 5 is not easily dislodged therefrom during the operation (FIGS. 1, 2 and 6). While a foam material is preferred, backing layer 40 may be constructed of any fabric or material possessing a texture in which clip 5 could securely bite into. Foam backing layer 40 extends beyond the periphery of much of tin foil layer 60 so that adhesive 55 applied to backing 40 may enhance the ability of electrode 20 to be affixed to the patient. Also, electrodes 20 are oriented on release web 10 such that tabs 30 are arranged along the central portion thereof, so that release web 10 may be folded back upon itself to expose tabs 30 for easy engagement therewith by a clip or the user's hand (FIGS. 3 and 4).

Foam backing layer 40 is made from a flexible polymeric foam material and includes a substantially rectangular body 41 and a projecting tab end or portion 47 (FIGS. 2 and 6). Tab end 47 is defined by an outer arcuate edge 48. Backing layer 40 further includes forward and rearward surfaces 51, 52, wherein forward surface 51 is completely coated with a pressure sensitive adhesive 55 (FIGS. 5 and 6).

Foam layer 40 should be of a material sufficiently soft and flexible that a lead clip will bite into it securely. Preferably, foam backing layer 40 is comprised of 6E closed cell polyethylene foam of about 1/32" in thickness. Other polymeric foam materials or soft, somewhat thicker materials which a lead clip can bite into would be equivalent.

Mounted on the adhesive side 51 of backing layer 40 is a tin foil layer 60, which also includes a substantially rectangular body 61 along with a projecting tab portion 67 (FIGS. 1, 5 and 6). Body 61 is of a reduced size relative to the size of body 41 of foam 40, and is interconnected to tab 67 by neck 64 (FIG. 1). Tin foil layer 60 is provided with forward and rearward surfaces 71, 72, and is attached to backing layer 40 by adhesive 55 such that rearward surface 72 is fixed to forward surface 51 of backing layer 40. Tab portion 67 of tin foil layer 60 corresponds in size and shape with tab portion 47 of backing layer 40. Tin foil layer 60 is mounted upon backing layer 40 such that tab portion 67 directly overlies tab portion 47 to thereby together define tab 30 of diagnostic electrode 20.

Body 61 of tin foil layer 60 is of a substantially smaller dimension, in length and width, as compared with body 41 of backing layer 40. When tin foil layer 60 is mounted on backing layer 40, it is substantially centered thereon, and thereby leaves around peripheral edge 62 of foil 60 a U-shaped border 44 of backing layer 40 (FIG. 1). Border 44 is coated with adhesive 55 to supplement the bonding of electrode 20 to the patient, as will be discussed below.

Coated on forward surface 71 of body 61 and neck 64 of tin foil layer 60 is a conductive gel 75. Gel 75 does not cover tab end 67 (FIG. 6). Conductive gel 75 is a sticky substance which, when electrode 20 is used, is pressed against the patient's body to mount diagnostic electrode 20 thereto and form the requisite contact therewith in order to gain the results of the test.

In the past, as previously discussed, the conductive gel provided the sole means by which diagnostic electrodes were affixed to the patients. This mounting arrangement is somewhat insecure and prone to accidental detaching of electrode 20 from the patient, particularly if the patient is hairy, sweaty, active, etc. However, by providing border 44 with adhesive 55, such that both conductive gel 75 and adhesive 55 are pressed against the patient, a secure mounting is achieved, even in difficult situations.

Diagnostic electrodes 20 are collectively mounted upon a release web 10, which is preferably sufficiently stiff and rigid to be easily handled. Preferably, it is made of a thin sheet of a relatively rigid plastic material. A most preferred material is a silicone coated polyester at a thickness of about 5 mils. Electrodes 20 are mounted with their forward surfaces 51, 71 pressed against release web 10, such that conductive gel 75 and adhesive 55 on border 44 positively engage release web 10 and affix electrodes 20 thereto.

Electrodes 20 are preferably mounted upon release web 10 in two rows 24, 25 (FIG. 1). Tabs 30 of the electrodes 20 in each row 24, 25 extend inwardly and are positioned along the central portion 11 of release web 10. Furthermore, rows 24, 25 are offset such that the longitudinal axis 27 of electrodes 20 in row 24 are aligned with outer edges 22, 23 of electrodes 20 in row 25 (FIGS. 1 and 2). Hence, tabs 30 of electrodes 20 in row 24 are juxtaposed and in contiguous relationship with tabs 30 of electrodes 20 in row 25, when electrodes 20 are mounted upon release web 10. Outer arcuate edges 31 of tabs 30, then, form an oscillating intersecting line 34, which is preferably generally sinusoidal in shape.

Extending along central portion 11 of release web 10 is a fold or score line 13 which is substantially parallel to rows 24, 25. Score line 13 is aligned with the middle of tabs 30 so that end portions 32 of tabs 30, from each row 24, 25, project beyond score line 13 an approximately equal distance.

To facilitate easy use of electrodes 20, release web 10 is folded back upon itself, along score line 13, so that the portion of rearward surface 15 of release web 10, to each side of score line 13, are placed adjacent each other in engaging relation (FIGS. 3 and 4). In this position, end portions of tabs 30 project above release web 10 to obviate the tedious procedure of peeling tab 30 from release web 10 and make it very easy to grasp or attach a clip thereto (FIGS. 3 and 4). Also, the offsetting of rows 24, 25 likewise offsets tabs 30, so that each tab may be easily engaged by clip 5 or the user's hand 2 without being blocked or overlapped by another tab.

Typically, after release web 10 has been folded back upon itself (as seen in FIGS. 3 and 4), clip 5 is attached to tab 30. Clip 5 thereby engages foam backing layer 40 and tin foil layer 60. Foam backing layer 40 provides a surface which can be securely gripped by clip 5, so that clip 5 is precluded from being inadvertently dislodged from tab 30 when electrode 20 is peeled from release web 10, transferred to the patient and properly positioned on the patient's body. This works especially well with so-called alligator clips, the teeth of which bite into the foam material.

Of course, it is understood that the above is merely a preferred embodiment of the invention, and that various other embodiments as well as many changes and alterations may be made without departing from the spirit and broader aspects of the invention as defined in the claims.

The embodiments of the invention in which an exclusive property or privilege is claimed are defined as follows:

1. A diagnostic electrode adapted to be affixed to a patient's body for medical testing, wherein said electrode comprises:

a flexible polymeric foam backing layer provided with a body and a tab portion projecting from one end thereof;

a tin foil layer provided with a body and a tab portion projecting from one end thereof, and bonded to said backing layer in an overlying relationship such that said tin foil tab portion overlies and is bonded to said backing layer tab portion to thereby define a tab of said electrode; and a sticky conductive gel coated on and adhered to a first surface of said body of said tin foil layer for engaging the patient's body;

a lead clip, having teeth, gripping said tab potion of said polymeric foam backing layer and said tin foil tab portion, said foam backing layer being sufficiently soft and flexible that said teeth of said clip bite into and securely grip said foam backing layer at said tab to preclude accidental dislodging of said clip from said tab portion of said foam backing layer or said tab portion of said tin foil layer which is bonded to said foam backing layer tab portion.

2. The diagnostic electrode of claim 1 in which said foam backing layer is provided with a first surface coated with an adhesive, whereby said adhesive bonds said tin foil layer to said backing layer; said body of said tin foil layer having length and width dimensions smaller than those of said body of said foam layer whereby said adhesive on said foam layer extends beyond said tin foil layer and adheres to the patient's body during use of said electrode.

3. The diagnostic electrode of claim 1 in which said body of said tin foil layer is mounted substantially centrally on said foam backing layer so that said backing layer with said adhesive defines a U-shaped border around said body of said tin foil layer.

4. An assembly for dispensing electrodes used in conducting medical tests, wherein said assembly comprises:

a release web provided with a fold line; and at least one electrode including a projecting tab, wherein said one electrode is mounted on said release web such that said tab overlies said fold line, whereby said release web may be folded along said fold line to expose said tab for easy access thereto.

5. The assembly of claim 4 which includes a plurality of said electrodes mounted on said release web in two rows such that said tabs of electrodes in each row face inwardly toward the other row of electrodes and such that said tabs of electrodes in one row ar offset from said tabs of electrodes in the other row such that said tabs are aligned along and overlying said fold line, whereby all of said tabs are exposed upon folding said release web along said fold line.

6. The assembly of claim 5 in which said tabs include an outer arcuate edge which collectively define a sinusoidal line when said electrodes are mounted on said release web.

7. The assembly of claim 6 in which said release web is of a material sufficiently stiff and thick to render it easily manipulated by a user.

8. The assembly of claim 5 in which said release web is of a material sufficiently stiff and thick to render it easily manipulated by a user.

9. The assembly of claim 4 in which said release web is of a material sufficiently stiff and thick to render it easily manipulated by a user.

10. An assembly for dispensing diagnostic electrodes used in conducting medical tests, wherein said assembly comprises:

a release web; and a plurality of diagnostic electrodes provided with adhesive coated bodies and non-adhesively coated projecting tabs adapted to be coupled with clips connected with diagnostic equipment, wherein said electrodes are mounted on said release web in two offset rows such that one surface of each tab faces said release web and said tabs are all aligned along a fold line which is parallel to said rows, whereby said release web may be folded on said fold line so as to expose a portion of said one surface of said tab for easy access thereto.

11. The assembly of claim 10 in which said tabs include outer arcuate edges which collectively define a sinusoidal line when said electrodes are mounted on said release web.

12. The assembly of claim 11 in which said release web is of a material sufficiently stiff and thick to render it easily manipulated by a user.

13. The assembly of claim 10 in which said release web is of a material sufficiently stiff and thick to render it easily manipulated by a user.

14. A method of affixing a diagnostic electrode to a patient's body for the running of a medical test, wherein said method comprises:

providing an assembly including a release web and a plurality of diagnostic electrodes mounted on said release web in two rows with one surface of each of said electrodes. facing said release web;

folding said release web such that a portion of said one surface of each of said electrodes is exposed;

attaching a clip, electrically coupled to diagnostic equipment, to said exposed portion of one removing said one electrode from said release web; and positioning said one electrode on the patient's body.

15. The method of claim 14 in which said provided assembly further mounts said rows of electrodes in offsetting relationship, such that said portions to be exposed are aligned along a line substantially parallel to said rows, whereby a single fold of said release web exposes all of said one surfaces of said electrode portions simultaneously.

16. The method of claim 15 in which said provided release web further includes a score line along which said release web is folded to expose said portion of said electrode, to thereby render said folding step easier to perform.

* * * * *

UNITED STATES PATENT AND TRADEMARK OFFICE
CERTIFICATE OF CORRECTION

PATENT NO. : 4,798,208

DATED : January 17, 1989

INVENTOR(S) : Adrian L. Faasse, Jr.

It is certified that error appears in the above-identified patent and that said Letters Patent is hereby corrected as shown below:

Column 5, Claim 3, Line 33:

"1" should be --2--.

Column 5, Claim 5, Line 53:

"ar" should be --are--.

Column 6, Claim 14, Line 45:

after "one" insert --electrode;--

Signed and Sealed this

Seventeenth Day of October, 1989

Attest:

DONALD J. QUIGG

Attesting Officer

Commissioner of Patents and Trademarks